United States Patent [19]

Reitan

[11] Patent Number: 5,749,855
[45] Date of Patent: May 12, 1998

[54] CATHETER PUMP

[76] Inventor: Oyvind Reitan, Villebradsvagen 10, s-226 53 Lund, Sweden

[21] Appl. No.: 387,941

[22] Filed: Feb. 27, 1995

[30] Foreign Application Priority Data

Sep. 2, 1992 [SE] Sweden ................. 92.02517

[51] Int. Cl.$^6$ .................................................. A61M 1/00
[52] U.S. Cl. ........................................ 604/151; 604/131
[58] Field of Search ............................ 604/151, 131, 604/93, 102, 267; 606/128; 415/900

[56] References Cited

U.S. PATENT DOCUMENTS

| | | | |
|---|---|---|---|
| 4,753,221 | 6/1988 | Kensey et al. | 604/151 X |
| 4,817,586 | 4/1989 | Wampler | 604/151 X |
| 4,919,647 | 4/1990 | Nash | 604/131 X |
| 4,944,722 | 7/1990 | Carriker et al. | 604/151 X |
| 4,969,865 | 11/1990 | Hwang et al. | 604/151 X |
| 5,163,910 | 11/1992 | Schwartz et al. | 604/151 |
| 5,169,378 | 12/1992 | Figuera . | |
| 5,320,627 | 6/1994 | Sorensen et al. | 606/128 |
| 5,324,177 | 6/1994 | Golding et al. | 604/151 X |

FOREIGN PATENT DOCUMENTS

| | | |
|---|---|---|
| 0364293 | 4/1990 | European Pat. Off. . |
| 0480102 | 4/1992 | European Pat. Off. . |
| 4124299 | 1/1992 | Germany . |
| WO 95/00186 | 1/1995 | WIPO .................. 604/151 |

*Primary Examiner*—Sam Rimell
*Attorney, Agent, or Firm*—Lerner, David, Littenberg, Krumholz & Mentlik

[57] ABSTRACT

Implantable catheter pumps are disclosed including a drive cable, with one end of the drive cable being connectable to a drive source, a collapsible drive propeller at the other end of the drive cable, with the collapsible drive propeller being adjustable between a closed configuration in which the collapsible drive propeller is collapsed upon the drive cable and an open configuration in which the collapsible drive propeller is expanded so as to be operative as an impeller, and a sleeve extending between one side of the collapsible drive propeller and the other side of the collapsible drive propeller with the sleeve being movable between configurations in which the collapsible drive propeller is in the open and closed configuration.

25 Claims, 4 Drawing Sheets

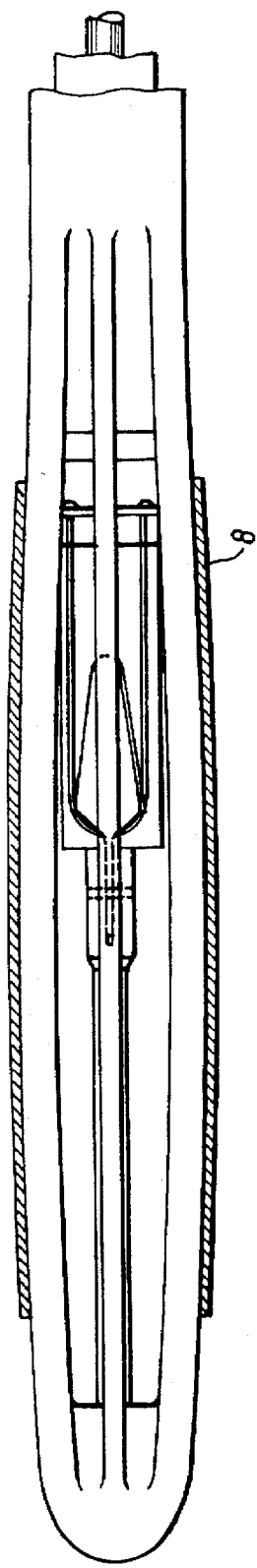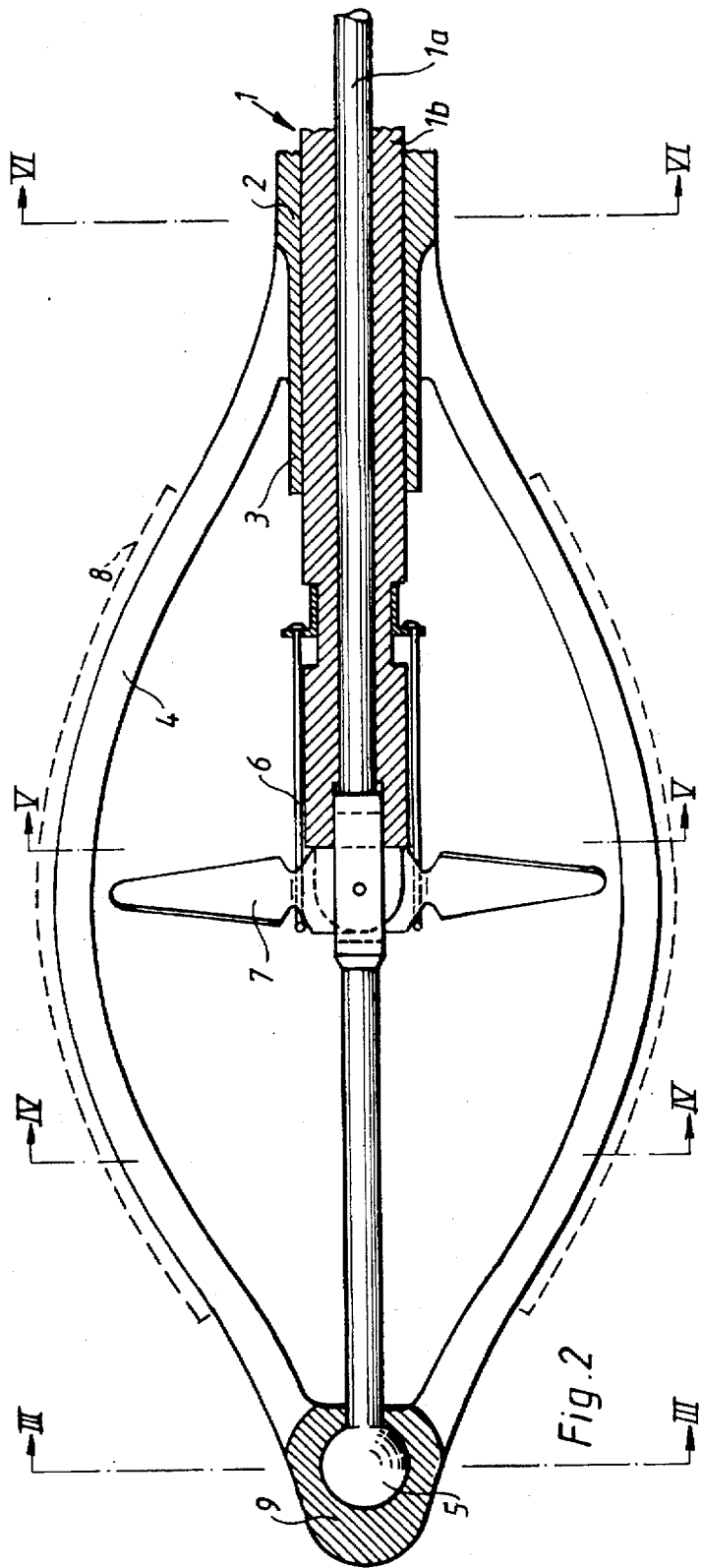
Fig.1
Fig.2

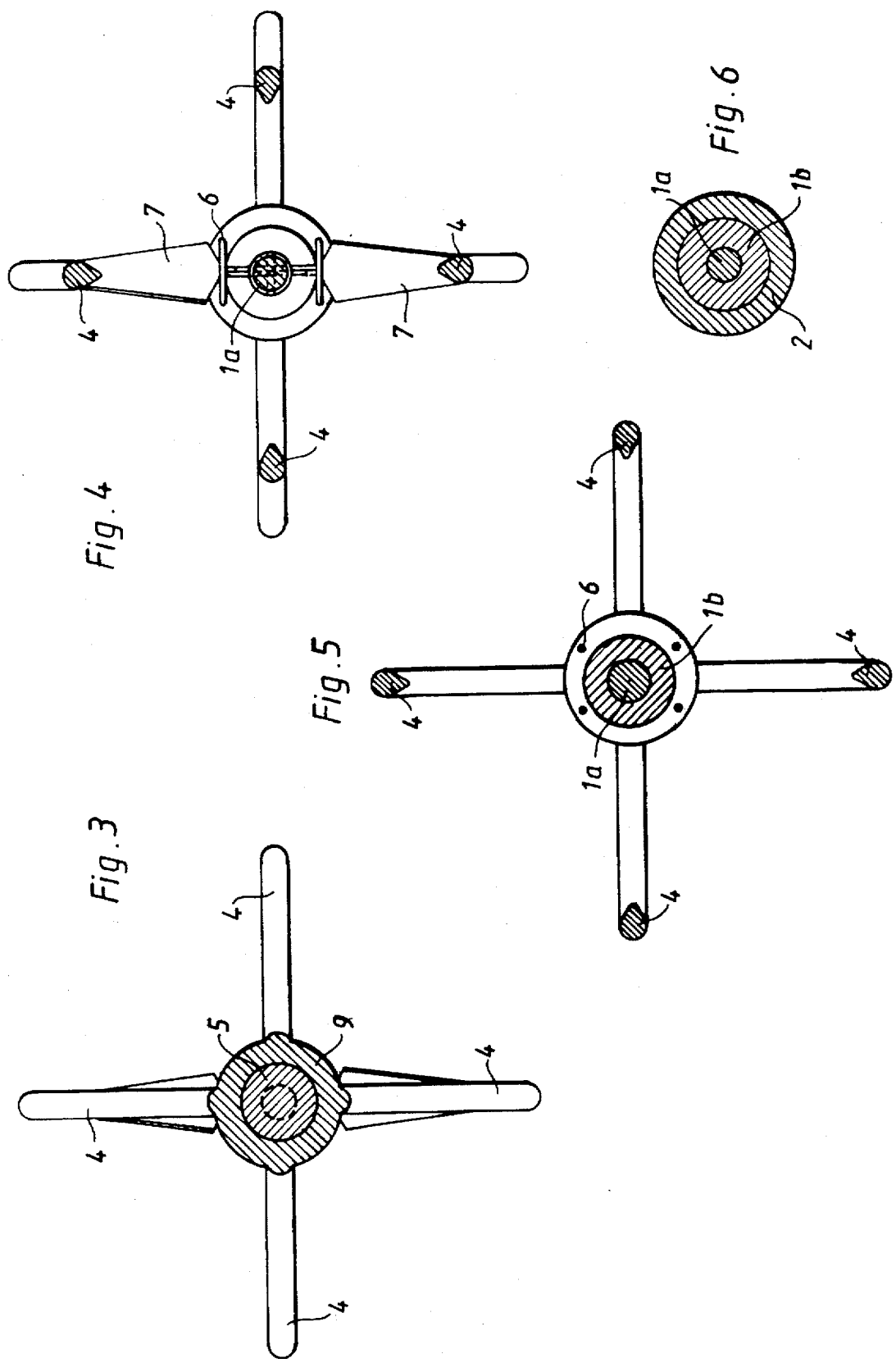

CATHETER PUMP

TECHNICAL FIELD

The present invention relates to a catheter pump intended for implantation and comprising an elongated sleeve through which a drive cable passes, the external end of which cable is connectable to an external drive source, the pump further comprising a drive rotor located in proximity to the inner end of the drive cable.

BACKGROUND OF THE INVENTION

No matter the cause, heart failure results in the heart pumping less blood to the body than that which the body requires in order to maintain vital functions.

There are three main causes of heart failure, these being:
reduced heart muscle function
valve failure (leakage or stenosis)
arrhythmia Reduced heart muscle function can have many causes. The most usual is due to a heart infarction which can lead to temporary or chronic failure. Examples of other causes of chronic or temporary failure are myocarditis (heart muscle inflammation), cardiomyopathy, metabolic diseases, poisonings, arrhythmia (irregular pulse) and many others. Also worth mentioning is temporary failure in patients after heart surgery and problems when stopping heart-lung-machine treatment.

Finally, a new group of patients should be mentioned who previously had chronic failure which nearly always was fatal but which now can be regarded as "temporary failure", i.e. those patients who are awaiting a heart transplant.

CALCULATION OF THE HEARTS MECHANICAL WORK

The mechanical heart work can be calculated from the following formula:

$$A = PV + \tfrac{1}{2} m v^2$$

and this represents the hearts work for each heartbeat.

PV hereby represents the pressure work per beat whilst $\tfrac{1}{2} m v^2$ denotes the blood acceleration work per beat.

With normal pump function and a normal blood pressure of 130/80, a beat volume of 70 ml and a heart frequency of 60 beats/minute, the heart generates approximately one joule per beat. The power is therefore 60 joules/60 seconds=1 Watt.

A typical failure situation is when the blood pressure sinks to 80/50 and the beat volume to 30 ml. In order to compensate for this the heart increases its frequency to, for example, 130 beats/minute. Nevertheless, the heart work is only approximately 25–50% of the normal and this corresponds to heart power of approximately 0,25–0,5 Watt.

TREATMENT OF HEART FAILURE

Traditional heart failure treatment has previously normally been a pharmacological treatment.

With help of drugs the heart's pump power can sometimes be increased to thereby overcome a failure situation. In this manner the heart's mechanical power is increased. This increase is however relatively small, for example 0,25–0,5 Watt and often works only for a short period of time.

MECHANICAL ASSISTANTS

The need to be able to overcome temporary or chronic heart failure has lead to many inventions, both pharmacological and mechanical. The increased need can partially be attributed to the increased activity in the heart field. In addition, there are those patients who previously would have died from "fatal failure" i.e. patients who are waiting for heart transplants and are in need of temporary extra pump power whilst waiting for the operation.

Pumps have been constructed which can assist the hearts own pump function or which can replace the heart entirely.

These more "drastic pumps" all have one thing in common, that being that they are normally surgically implanted in the patient with the damaging side effects which this implies.

The need for simpler "non-surgical" pumps is therefore great.

PRESENT "NON-SURGICAL" PUMPS

In 1968 the aorta balloon-pump was launched on the market and since then it has been in use throughout the entire western world. This pump has good and poor properties:

good properties:
  it is easy to use
  it is easily introduced via an insertion in the arteria femoralis in the groin
  it increases the hearts own circulation (coronary throughflow)
  it increases the peripheral blood pressure poor properties:
  it reduces the peripheral blood circulation and therefore has a restricted period of use
  it gives only a small increase of the minute volume (maximum approximately 30%)
  gives non-physiological pulses
  is dependent on the heart having a certain minimal function

PUMPS USING AN ARCHIMEDES SCREW (HEMOPUMP)

In recent years an American pump has been available under the name "Hemopump". As pump principle the pump makes use of a rotary Archimedes screw which, via a metal cable in a catheter, is driven by an external electric motor. The catheter is inserted in the groin and introduced into the arteria femoralis with help of a small surgical insertion. It is thereafter led up into the aorta and a flexible needle is introduced through the aorta valves and sucks out blood from the left chamber to the aorta.

The catheter has been made as narrow as possible. The needle in the left chamber has a diameter of approximately 7 mm and the Archimedes screw a diameter of around 3 mm.

At maximum speed, i.e. 25 000 rpm, it can maintain approximately 80% of the normal minute volume under continuous operation, i.e. non-pulsing.

Good properties:
  easy to insert
  good properties at maximum speed
  can maintain almost normal minute volume at maximum speed Poor properties:
  risk of overheating because of high rotational speed
  lubrication problems for the same reason
  non-physiological (non-pulsing) operation
  risk of a short life span because of wear
  increases the afterload

DESCRIPTION OF THE PRESENT INVENTION

The present invention thus relates to a catheter pump intended for implantation and comprising an elongated sleeve through which a drive cable passes, the external end of which cable is connectable to an external drive source, the pump further comprising a drive rotor located in proximity to the inner end of the drive cable. More precisely, the pump is characterized in that said drive rotor is in the form of an outwardly-foldable propeller.

Because of the outwardly-foldable propeller, the catheter can be made very narrow, which is advantageous during introduction into the blood stream, but nevertheless provides a powerful flow effect in its outwardly-folded condition.

The catheter, which should have a maximum diameter of 3–5 mm, is introduced according to the normal Seldinger technique in the groin (arteria femoralis) and led up to the aorta to the desired position. The best position would be in the ascending aorta just above the aortic valve.

The propeller can be placed in an arbitrary region of the aorta and can also be introduced into the left chamber.

In order to avoid the propeller, which can have a diameter of 1–2 cm, damaging the aorta, as described in the following the catheter should be provided with a lattice or bars which shield the propeller.

When introduced into the left chamber, the bars can be provided with an elastic rubber sheath which prevents damage to the vital parts of the heart and which can also increase the pressure effect.

In order to avoid thromboembolismic complications, the pump or parts thereof can be heparinized.

The pump is primarily intended for use in failure of the left chamber, but it is also conceivable that it be used for failure in the right chamber.

It is conceivable that the pump be introduced via the vein system in the neck and into the right chamber or possibly in the arteria pulmonalis and thus with reversed rotational direction.

The above mentioned bars are suitably in the form of an expandable part adjacent the propeller. This part can be in the form of filaments extending in the longitudinal direction of the sleeve.

Preferably, the forward ends of these filaments are united at a common attachment which is arranged to be able to be displaced towards the propeller during the formation of a filament cage around the propeller. Said movement can be achieved through the attachment being attached to the drive cable, which is accordingly arranged to be axially displaceable for expansion of the filament cage.

Adjustment of the propeller also suitably takes place with help of the drive cable. It can thus be arranged to be folded out with the help of the drive cable, hence the drive cable being axially displaceable.

The drive cable can be in the form of a compact cable. Alternatively, it can be in the form of an inner core with an outer sleeve axially displaceable with respect to the core.

With the latter embodiment a link mechanism can be attached to the propeller and to the core and outer sleeve respectively of the drive cable, the mechanism having such a construction that the propeller is folded outwardly by a relative sliding between the core of the cable and the outer sleeve.

As mentioned above, the expandable part can be surrounded by a sleeve or a tube of an elastic material such as rubber or similar.

Preferably, the drive cable is arranged to be rotated at a number of revolutions which is less than 10 000 rpm, preferably in the order of 3–5 000 rpm.

In its folded out condition, the propeller should have a work diameter of 10–20 mm, preferably about 15 mm.

The propeller is suitably arranged to be subjected to an effective pumping power in the order of 0.25–1 Watt, preferably about 0.5 Watt.

The particularly simple embodiment of the pump according to the invention is achieved if the propeller consists of a number of propeller blades individually carried on the drive axle which are arranged to be folded outwardly to their operational position due to centrifugal and/or pumping force during rotation of the drive axle.

The propeller blades are hereby suitably made to abut a propeller support mounted on the drive axle when the propeller blades are in their operational position.

Alternatively, in their operational position, the propeller blades can be locked between a propeller support mounted on the drive axel and a sleeve rotatable with the drive axle.

ADVANTAGES OF THE INVENTION

The entire construction can be made very thin for insertion and removal respectively, maximum diameter 3–5 mm.

Slower rotation compared with other rotating pumps because of larger propeller diameter (less than 10 000 rpm, suitably 3–5 000 rpm).

Less tendency to overheat.

Reduced lubrication problems.

Increased life span.

Because of the strong flow power it is conceivable to provide a pulsed operation synchronized to the heart's activity, for example QRS-controlled.

Should reversed pulsation be required, the pump can reverse its direction of rotation.

DESCRIPTION OF THE DRAWINGS

FIG. 1 is intended to illustrate the external dimensions of a catheter pump according to a first embodiment of the invention (scale 5:1).

FIG. 2 shows the same pump in its operational position.

FIGS. 3–6 show sections according to lines III—III, IV—IV, V—V and VI—VI respectively in FIG. 2.

Finally.

PREFERRED EMBODIMENTS OF THE INVENTION

Figure 7:
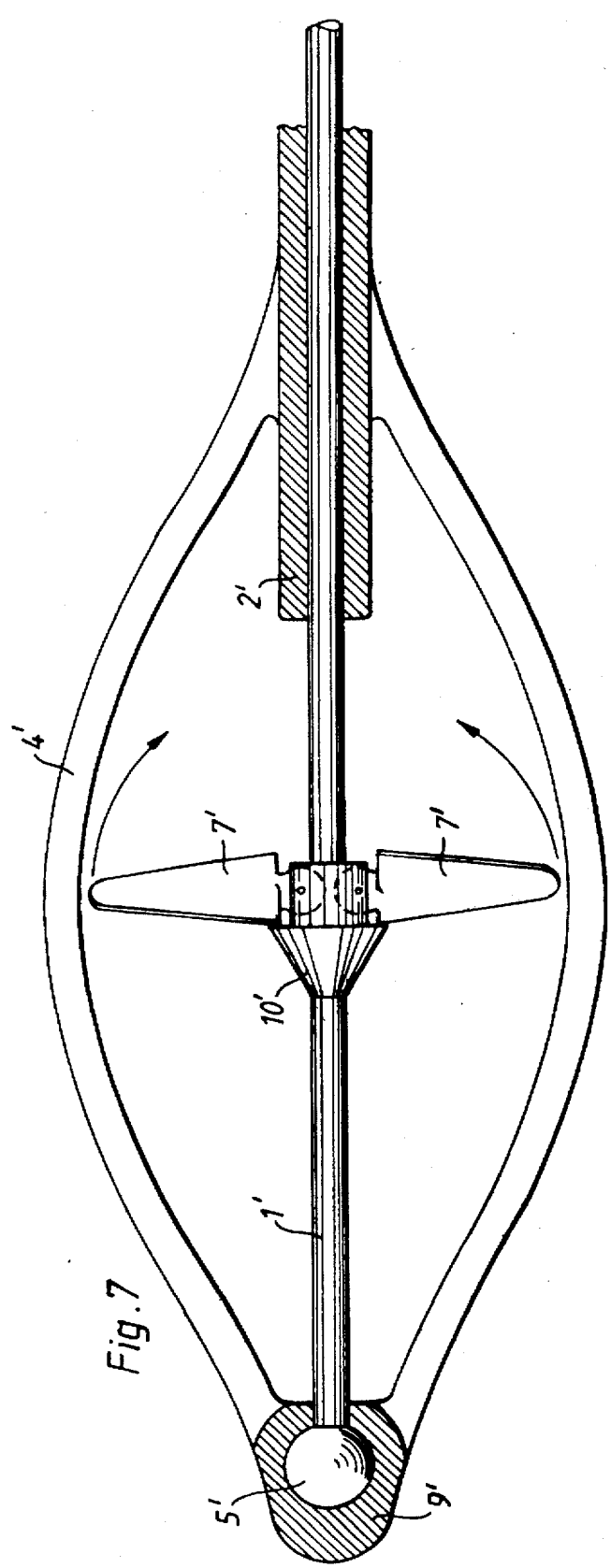
FIG. 7 schematically shows a second embodiment of the invention in its operational position.

A first embodiment of the catheter pump according to the invention is shown in FIG. 2 in its operational position. The pump comprises innermost a drive cable 1 which consists of an inner part 1a and an outer part 1b. The drive cable 1 is surrounded by an outer sleeve 2 which at its forward end merges into a cylindrical region 3 together with a plurality of filaments 4. At its forward extremity, the drive cable 1 terminates with a round nipple 5 which serves both as a bearing and as an attachment for the filaments 4. By means of a link mechanism 6, an outwardly foldable propeller 7 is secured to the inner drive axle 1a. The link mechanism 6 is schematically shown and can be modified in various ways in order to achieve the desired function. Finally, the dashed lines 8 indicate that the lattice cage formed by the filaments 4 can be surrounded by an outer elastic sleeve of, for example, rubber.

The filaments 4 have been expanded to the position shown in FIG. 2 by means of a relative displacement between the drive cable 1 and its sleeve 2. At the same time the propeller 7 has been folded outwards with help of the link mechanism 6 by means of a relative displacement between the two parts 1a and 1b of the drive cable 1.

FIG. 3 shows a section along line III—III in FIG. 2, i.e. a section through the bearing nipple 5 and the attachment part 9 of the filaments 4.

FIG. 4 shows a section along line IV—IV in FIG. 2 and here it can be seen how the inner axle 1a can be surrounded by four filaments 4. This number can of course be varied.

FIG. 5 shows a section along line V—V in FIG. 2 and illustrates how the inner axle 1a is surrounded by an outer axle 1b and the cylindrical extension 3 of the sleeve 2. These are all surrounded by the lattice cage formed by the filaments 4.

FIG. 6 shows a section along line VI—VI in FIG. 2 and illustrates how the inner axle 1a is surrounded by the outer axle 1b and the sleeve 2.

Figure 8:
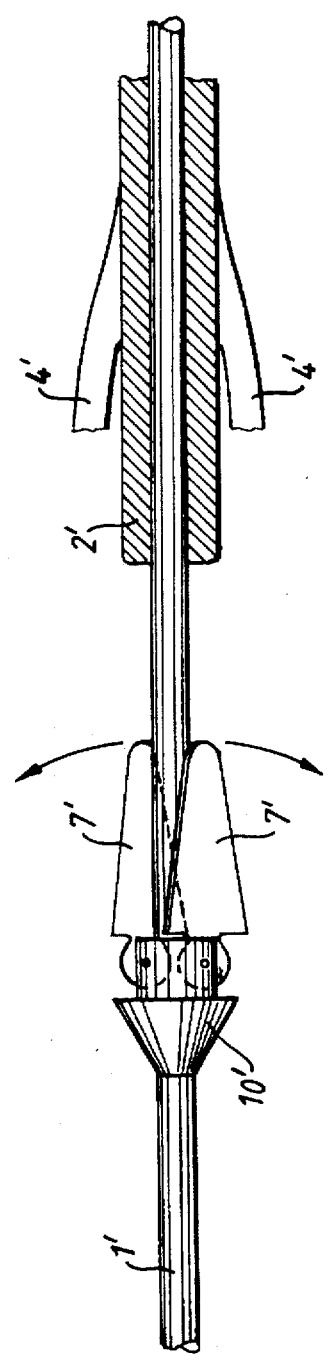
FIG. 8 shows a part of FIG. 7 in rest position.

FIGS. 7 and 8 schematically show a simplified embodiment of the catheter pump according to the invention. In principle, however, it corresponds to the embodiment according to FIGS. 1–6, and thus the same figure reference numeral have been used for corresponding parts, though with the addition of a prime. The drive axle 1' here consists of a single solid part surrounded by the sleeve 2'. The filaments 4' are in the same manner as described above secured to both the sleeve 2' and to a common forward section 9', which also serves as a bearing for the bearing nipple 5'. The main difference with respect to the above described embodiment is that the blades or propeller 7' are here individually carried on a support part 10'.

In FIG. 8 the blades are shown in their inwardly folded position. As soon as rotation is started they are automatically folded outwardly to their operational position shown in FIG. 7. This occurs due to both the centrifugal force and because the blades are so shaped that due to the pumping forces they are driven outwardly to their operational position. Folding in of the blades 7' can thus take place by reversing the rotational direction of the axle 1'.

Figure 9:
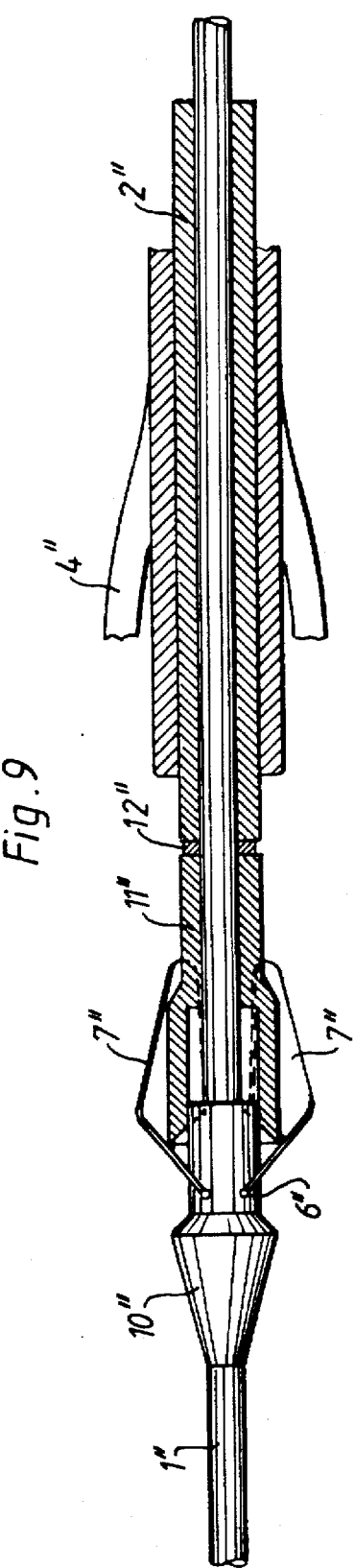
FIG. 9 shows a part of a third embodiment in its rest position.
Figure 10:
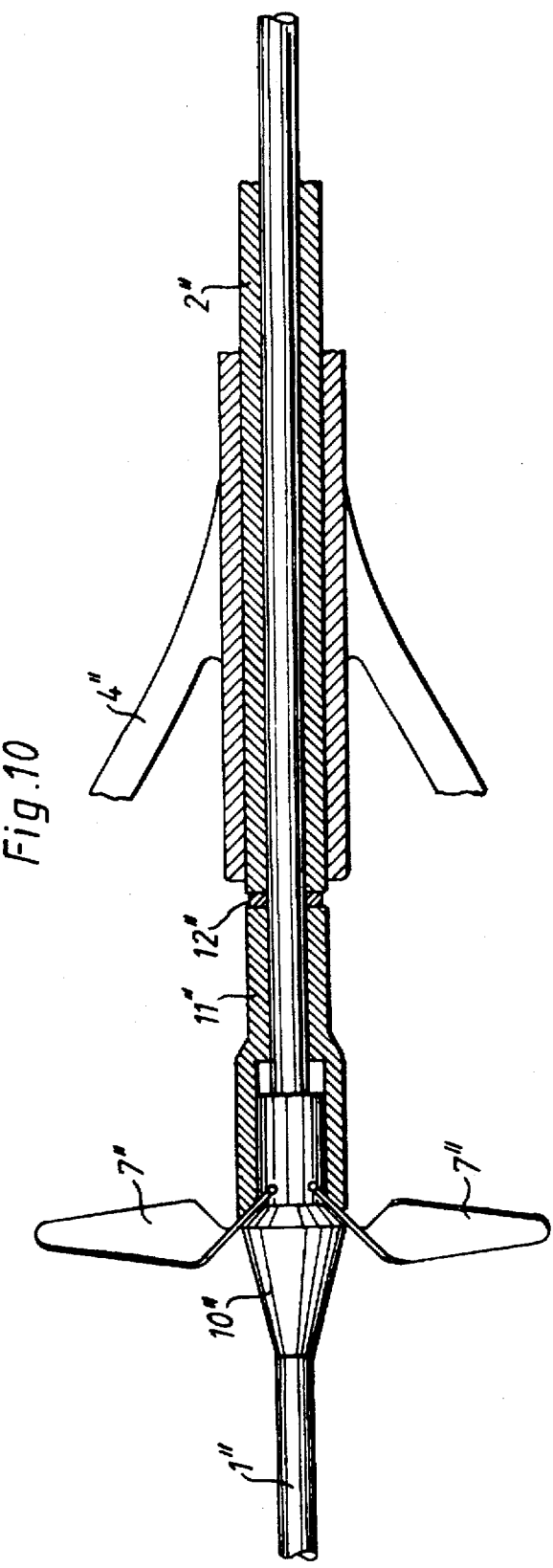
FIG. 10 shows the part according to FIG. 9 in its operational position.

FIGS. 9 and 10 show a further modification of the catheter pump according to the invention. This embodiment also corresponds to the above described, and so the same figure reference numerals have been used for corresponding components, though with the addition of a double prime. The inner drive axle is thus denoted by 1", a propeller support by 10" and the propeller by 7". As with the above described embodiments, the inner drive axle 1" is surrounded by an outer sleeve 2". In this embodiment a rotating displaceable cylinder 11" has been added which slides against the forward face of the sleeve 2" which is provided with a slide bearing 12". The propeller 7" is carried on the inner drive axle 1" by means of a bearing or link mechanism 6". A displacement of the drive axle 1" to the right in FIG. 9 hereby leads to the propeller 7" being locked between the propeller support 10" and the cylinder 11" as shown in FIG. 10.

Naturally, the invention is not restricted to the above described and schematically illustrated embodiments but can be varied within the scope of the appended claims. For example, both the shape and function of the various illustrated components can be varied.

Should lubrication for the drive cable 1 be necessary, this can be achieved with help of a physiologically suitable salt solution under pressure, possible during addition of heparin, citrate and/or streptokinase. Heparin and citrate hereby prevent coagulation and streptokinase penetrates into fibrin in the space around the drive cable.

I claim:

1. An implantable catheter pump for pumping blood comprising a drive cable including a first end and a second end, said first end of said drive cable being connectable to a drive source, a collapsible drive propeller attached proximate to said second end of said drive cable, means for adjusting said collapsible drive propeller between a closed configuration in which said collapsible drive propeller is collapsed upon said drive cable and an open configuration in which said collapsible drive propeller is expanded so as to be operative as an impeller, and elongated sleeve means extending between a first location on said drive cable on a first side of said collapsible drive propeller and a second location on said drive cable on a second side of said collapsible drive propeller thereby surrounding said collapsible drive propeller, said elongated sleeve means movable between a first configuration proximate to said drive cable when said collapsible drive propeller is in said closed configuration and a second configuration expanded about said drive cable for accommodating said collapsible drive propeller in said open configuration said sleeve means further having an open configuration thereby permitting said blood to flow through said sleeve means and said collapsible drive propeller when said collapsible drive propeller is in said open configuration.

2. The implantable catheter pump of claim 1 wherein said elongated sleeve means comprises a plurality of filament members.

3. The implantable catheter pump of claim 2 wherein said first location on said drive cable comprises said second end of said drive cable.

4. The implantable catheter pump of claim 1 wherein said elongated sleeve means is attached to said drive cable at said first location, and said drive cable is axially displaceable to expand said elongated sleeve means from said first configuration to said second configuration around said collapsible drive propeller.

5. The implantable catheter pump of claim 1 wherein said drive cable is axially displaceable, and said collapsible drive propeller is adjustable between said closed configuration and said open configuration by axial displacement of said drive cable.

6. The implantable catheter pump of claim 1 wherein said drive cable comprises an inner core and an outer reinforcement surrounding said inner core, said outer reinforcement being axially displaceable with respect to said inner core.

7. The implantable catheter pump of claim 6 including linking means connecting said collapsible drive propeller to said outer reinforcement of said drive cable, said collapsible drive propeller being connected to said inner core of said drive cable, whereby said collapsible drive propeller can be adjusted between said closed configuration and said open configuration by relative displacement between said inner core and said outer reinforcement.

8. The implantable catheter pump of claim 1 wherein said elongated sleeve means includes an outer covering.

9. The implantable catheter pump of claim 8 wherein said outer covering comprises an elastic material.

10. The implantable catheter pump of claim 9 wherein said elastic material comprises rubber.

11. The implantable catheter pump of claim 1 wherein said drive means is adapted to rotate said drive cable at a rate of less than 10,000 rpm.

12. The implantable catheter pump of claim 11 wherein said drive means is adapted to rotate said drive cable at a rate of between 3,000 and 5,000 rpm.

13. The implantable catheter pump of claim 11 wherein said collapsible drive propeller, when in said closed configuration, has a diameter of between about 10 and 20 mm.

14. The implantable catheter pump of claim 13 wherein said collapsible drive propeller, when in said closed configuration, has a diameter of about 15 mm.

15. The implantable catheter pump of claim 1 wherein said drive source is adapted to subject said collapsible drive propeller to an active pumping power of between about 0.25 and 1 watts.

16. The implantable catheter pump of claim 15 wherein said drive source is adapted to subject said collapsible drive propeller to an active pumping power of about 0.5 watts.

17. The implantable catheter pump of claim 1 wherein said collapsible drive propeller comprises a plurality of blade members pivotably mounted with respect to said drive cable wherein said collapsible drive propeller is adjustable from said closed configuration to said open configuration by rotation of said drive cable.

18. The implantable catheter pump of claim 17 including a propeller support member mounted on said drive cable abutting said plurality of blade members when said collapsible drive propeller is in said open configuration.

19. The implantable catheter pump of claim 18 including bushing means fixedly mounted on said drive cable on said side of said drive cable opposite to said propeller support member whereby said plurality of blade members are locked between said propeller support means and said bushing means when said collapsible drive propeller is in said open configuration.

20. An implantable catheter pump for pumping blood comprising a drive cable including a first end and a second end, said first end of said drive cable being connectable to a drive source, a collapsible drive propeller attached proximate to said second end of said drive cable, means for adjusting said collapsible drive propeller between a closed configuration in which said collapsible drive propeller is collapsed upon said drive cable and an open configuration in which said collapsible drive propeller is expanded so as to be operative as an impeller, and elongated sleeve means comprising a plurality of filament members extending between a first location on said drive cable on a first side of said collapsible drive propeller and a second location on said drive cable on a second side of said collapsible drive propeller thereby surrounding said collapsible drive propeller, said elongated sleeve means movable between a first configuration proximate to said drive cable when said collapsible drive propeller is in said closed configuration and a second configuration expanded about said drive cable for accommodating said collapsible drive propeller in said open configuration.

21. The implantable catheter pump of claim 20 wherein said first location on said drive cable comprises said second end of said drive cable.

22. An implantable catheter pump for pumping blood comprising a drive cable including a first end and a second end, said first end of said drive cable being connectable to a drive source, a collapsible drive propeller attached proximate to said second end of said drive cable, means for adjusting said collapsible drive propeller between a closed configuration in which said collapsible drive propeller is collapsed upon said drive cable and an open configuration in which said collapsible drive propeller is expanded so as to be operative as an impeller, and elongated sleeve means extending between a first location on said drive cable on a first side of said collapsible drive propeller and a second location on said drive cable on a second side of said collapsible drive propeller thereby surrounding said collapsible drive propeller, said elongated sleeve means movable between a first configuration proximate to said drive cable when said collapsible drive propeller is in said closed configuration and a second configuration expanded about said drive cable for accommodating said collapsible drive propeller in said open configuration, said elongated sleeve means being attached to said drive cable at said first location, and said drive cable being axially displaceable to expand said elongated sleeve means from said first configuration to said second configuration around said collapsible drive propeller.

23. An implantable catheter pump for pumping blood comprising a drive cable including a first end and a second end, said first end of said drive cable being connectable to a drive source, a collapsible drive propeller attached proximate to said second end of said drive cable, means for adjusting said collapsible drive propeller between a closed configuration in which said collapsible drive propeller is collapsed upon said drive cable and an open configuration in which said collapsible drive propeller is expanded so as to be operative as an impeller, and elongated sleeve means extending between a first location on said drive cable on a first side of said collapsible drive propeller and a second location on said drive cable on a second side of said collapsible drive propeller thereby surrounding said collapsible drive propeller, said elongated sleeve means movable between a first configuration proximate to said drive cable when said collapsible drive propeller is in said closed configuration and a second configuration expanded about said drive cable for accommodating said collapsible drive propeller in said open configuration, said drive cable being axially displaceable, and said collapsible drive propeller being adjustable between said closed configuration and said open configuration by axial displacement of said drive cable.

24. An implantable catheter pump for pumping blood comprising a drive cable including a first end and a second end, said drive cable comprising an inner core and an outer reinforcement surrounding said inner core, said outer reinforcement being axially displaceable with respect to said inner core, said first end of said drive cable being connectable to a drive source, a collapsible drive propeller attached proximate to said second end of said drive cable, means for adjusting said collapsible drive propeller between a closed configuration in which said collapsible drive propeller is collapsed upon said drive cable and an open configuration in which said collapsible drive propeller is expanded so as to be operative as an impeller, and elongated sleeve means extending between a first location on said drive cable on a first side of said collapsible drive propeller and a second location on said drive cable on a second side of said collapsible drive propeller thereby surrounding said collapsible drive propeller, said elongated sleeve means movable between a first configuration proximate to said drive cable when said collapsible drive propeller is in said closed configuration and a second configuration expanded about said drive cable for accommodating said collapsible drive propeller in said open configuration.

25. The implantable catheter pump of claim 24 including linking means connecting said collapsible drive propeller to said outer reinforcement of said drive cable, said collapsible drive propeller being connected to said inner core of said drive cable, whereby said collapsible drive propeller can be adjusted between said closed configuration and said open configuration by relative displacement between said inner core and said outer reinforcement.

* * * * *

UNITED STATES PATENT AND TRADEMARK OFFICE
CERTIFICATE OF CORRECTION

| | | |
|---|---|---|
| PATENT NO. | : | 5,749,855 |
| DATED | : | May 12, 1998 |
| INVENTOR(S) | : | Oyvind Reitan |

It is certified that error appears in the above-identified patent and that said Letters Patent is hereby corrected as shown below:

On title page, item

[22] Delete "Filed: Feb. 27, 1995" and insert therefor --PCT Filed: August 19, 1993

[86] PCT No.: PCT/SE93/00690
§ 371 Date: February 27, 1995
§ 102(e) Date: February 27, 1995

[87] PCT Pub. No.: WO 94/05347
PCT Pub. Date: March 17, 1994--

Column 7, line 1, delete "11" and insert therefor --1--.

Signed and Sealed this

Third Day of November, 1998

Attest:

BRUCE LEHMAN

*Attesting Officer*      *Commissioner of Patents and Trademarks*